(12) United States Patent
Kadbi et al.

(10) Patent No.: US 12,092,716 B2
(45) Date of Patent: Sep. 17, 2024

(54) SYNTHETIC FOUR-DIMENSIONAL COMPUTED TOMOGRAPHIC IMAGE GENERATION

(71) Applicant: KONINKLIJKE PHILIPS N.V., Eindhoven (NL)

(72) Inventors: Mohammad Hossein Kadbi, Houston, TX (US); Lizette Warner, Arlington, TX (US); Marinus Johan Kruiskamp, Zaltbommel (NL)

(73) Assignee: Koninklijke Philips N.V., Eindhoven (NL)

(*) Notice: Subject to any disclaimer, the term of this patent is extended or adjusted under 35 U.S.C. 154(b) by 327 days.

(21) Appl. No.: 17/638,206

(22) PCT Filed: Aug. 28, 2020

(86) PCT No.: PCT/EP2020/074095
§ 371 (c)(1),
(2) Date: Feb. 25, 2022

(87) PCT Pub. No.: WO2021/038053
PCT Pub. Date: Mar. 4, 2021

(65) Prior Publication Data
US 2022/0299587 A1    Sep. 22, 2022

Related U.S. Application Data

(60) Provisional application No. 62/893,890, filed on Aug. 30, 2019.

(30) Foreign Application Priority Data

Sep. 23, 2019  (EP) ..................... 19198834

(51) Int. Cl.
*G01R 33/56* (2006.01)
*A61B 5/00* (2006.01)
(Continued)

(52) U.S. Cl.
CPC ........ *G01R 33/5608* (2013.01); *A61B 5/0036* (2018.08); *A61B 5/055* (2013.01);
(Continued)

(58) Field of Classification Search
CPC ............ G01R 33/5608; G01R 33/4812; G01R 33/4828; G01R 33/567; A61B 5/0036;
(Continued)

(56) References Cited

FOREIGN PATENT DOCUMENTS

| JP | 2008228802 A | 10/2008 |
|---|---|---|
| JP | 2009022319 A | 2/2009 |

(Continued)

OTHER PUBLICATIONS

Freedman JN, Bainbridge HE, Nill S, Collins DJ, Kachelrieß M, Leach MO, McDonald F, Oelfke U, Wetscherek A. Synthetic 4D-CT of the thorax for treatment plan adaptation on MR-guided radiotherapy systems. Phys Med Biol. May 23, 2019;64(11): (Year: 2019).*

(Continued)

*Primary Examiner* — Patrick Fernandes
*Assistant Examiner* — Nicholas A Robinson (57) ABSTRACT

Disclosed herein is a medical system (100, 300, 500) comprising a processor (104) configured for controlling the medical system and a memory (110) for storing machine executable instructions. Execution of the instructions causes the processor to receive (200) four-dimensional Dixon magnetic resonance image data (122). The four-dimensional Dixon magnetic resonance imaging data is T1 weighted. The four-dimensional Dixon magnetic resonance image data is synchronized to a respiratory signal (124). Execution of the instructions further causes the processor to reconstruct (202) synthetic four-dimensional computed tomographic image data (12) from the four-dimensional Dixon magnetic reso- (Continued)

nance imaging data. The four-dimensional Dixon magnetic resonance imaging data is synchronized to the respiratory signal.

14 Claims, 6 Drawing Sheets

(51) Int. Cl.
    *A61B 5/055*      (2006.01)
    *A61N 5/10*      (2006.01)
    *G01R 33/48*      (2006.01)
    *G01R 33/567*      (2006.01)

(52) U.S. Cl.
    CPC ....... *A61N 5/1037* (2013.01); *G01R 33/4812* (2013.01); *G01R 33/4828* (2013.01); *G01R 33/567* (2013.01); *A61N 2005/1055* (2013.01)

(58) Field of Classification Search
    CPC .................. A61B 5/055; A61N 5/1037; A61N 2005/1055; A61N 5/1049; A61N 5/1068; A61N 5/1039
    See application file for complete search history.

(56) References Cited

FOREIGN PATENT DOCUMENTS

| JP | 2015516259 A | 6/2015 |
|----|--------------|--------|
| WO | 2015103184 A1 | 7/2015 |

OTHER PUBLICATIONS

Joshua N. Freedman et al "Synthetic 4D-CT of the Thorax for Treatment Plan Adaptation On MR Guided Radiotheraphy Systems" Physics in Med. and Bio. vol. 64, No. 11, May 23, 2019 p. 115005.

Menten Martin J. et al "MRI-Guided Lung SBRT: Present and Future Developments" Physica Medica vol. 44, Feb. 25, 2017 p. 139-149.

International Search Report and Written Opinion From PCT/EP2020/074095 Mailed Nov. 25, 2020.

Al-Ward et al "The Development of a 4D Treatment Planning Methodology to Simulate the Tracking of Central Lung Tumors in a MRI-Linac" J. Appl. Clin. Med Phys 2018 p. 145-155.

Boyle et al "Mapping Motion for 4D-MRI to 3D-CT for Use in 4D Dose Calculations: A Technical Feasiblilty Study" Med. Phys. 40(6) Jun. 2013.

Freedman, Joshua & Bainbridge, H. & Wetscherek, Andreas & Collins, David & Nill, Simeon & Dunlop, Alex & Kachelrieß, Marc & Leach, M. & Mcdonald, Fiona & Oelfke, Uwe. (2018). PO-0959: Dosimetric Evaluation of Midposition Pseudo-CT for MR-only Lung Radiotherapy Treatment planning. Radiotherapy and Oncology. 127. S526-8527. 10.1016/S0167-8140(18)31269-6.

Muller et al "A Phantom Study to Create Synthetic CT From Orthogonal Two-Diemensional Cine MRI and Evaluate the Effect of Irregular Breathing".

Yang et al "Respiratory Phase-Matched MR-Based Attenuation Correction for Four-Dimensional PET in PET/MRI: A Feasilbility Study" Proc. Intl. Soc. Mag. Reson. Med 25 (2017).

* cited by examiner

SYNTHETIC FOUR-DIMENSIONAL COMPUTED TOMOGRAPHIC IMAGE GENERATION

CROSS REFERENCE TO RELATED APPLICATIONS

This application is a U.S. national phase application of International Application No. PCT/EP2020/074095 filed on Aug. 28, 2020, which claims the benefit of U.S Provisional Application Ser. No. 62/893890 filed Aug. 30, 2019 and EP Application Serial No. 19198834.3 filed on Sep. 23, 2019 and is incorporated herein by reference.

FIELD OF THE INVENTION

The invention relates to Magnetic Resonance Imaging, in particular to generation of synthetic computed tomographic images from magnetic resonance images.

BACKGROUND OF THE INVENTION

Computer tomography (CT) images are useful for radiotherapy planning. CT image measure the three-dimensional absorption of X-rays by the body. The images can be expressed in terms of a Hounsfield units or as a spatial dependent electron density map. One of these values are typically used by radiotherapy planning software to estimate the absorption of ionizing radiation for radiotherapy. A difficulty in using CT for radiotherapy planning is firstly that it exposes the subject to additional radiation. Another difficulty is that CT is excellent in imaging hard or dense tissues such as bone, but it does not differentiate between different type of soft tissue as well as magnetic resonance imaging (MRI). Commonly during radiation therapy planning both a CT image and an MRI image will be acquired. The combination of the two enable excellent estimation of radiation absorbed by the subject as well as the ability to differentiate different types of tissue such as healthy tissue from tumors.

International patent application publication WO 2015/103184 A1 discloses systems and methods directed to adaptive radiotherapy planning are provided. In some aspects, the disclosed system and method include producing synthetic images from magnetic resonance data using relaxometry maps. The method includes applying corrections to the data and generating relaxometry maps therefrom. In other aspects, a method for adapting a radiotherapy plan is disclosed. The method includes determining an objective function based on dose gradients from an initial dose distribution, and generating an optimized plan based on updated images, using aperture morphing and gradient maintenance algorithms without need for organ-at-risk contouring. In yet other aspects, a method for obtaining 4D MR imaging using a temporal reshuffling of data acquired during normal breathing, a method for deformable image registration using a sequentially applied semi-physical model regularization method for multimodality images, and a method to generate 4D plans using an aperture morphing algorithm based on 4D CT or 4D MR imaging are disclosed.

SUMMARY OF THE INVENTION

The invention provides for a medical system, a computer program product, and a method in the independent claims. Embodiments are given in the dependent claims.

Embodiments provide for an improved method of producing synthetic four-dimensional computed tomographic data from four-dimensional Dixon magnetic resonance data that is T1 weighted. The four-dimensional Dixon magnetic resonance data is synchronized to a respiratory signal and resulting in synthetic four-dimensional computed tomographic data. The respiratory signal could for example be a respiratory phase or respiratory amplitude. The respiratory signal may then be used, for example, to improve control of a radiotherapy system.

Dixon magnetic resonance imaging acquires the magnetic resonance imaging data at various phases so that a water image can be generated and a fat image can be generated. This enables superior segmentation of the images and therefore enables higher quality synthetic CT images to be produced.

WO 2015/103184 A1 teaches away from the use of Dixon magnetic resonance images. It notes in par. 33 that the misregistration of multi-echo Dixon image can confound image segmentation, resulting in blurred structure boundaries.

In one aspect the invention provides for a medical system that comprises a processor configured for controlling the medical system. The medical system further comprises a memory for storing machine-executable instructions. Execution of the instructions causes the processor to receive four-dimensional Dixon magnetic resonance image data. The four-dimensional Dixon magnetic resonance image data is T1 weighted. The four-dimensional Dixon magnetic resonance image data is synchronized to a respiratory signal. The synchronization to the respiratory signal may be accomplished in different ways. For example, the respiratory signal could be measured using self-navigation in k-space data, a navigator, a respiratory balloon measurement (measurement of an oxygen mask reservoir), an optical measurement of breathing with a camera system and/or respirator belt. In one example there may be a measured signal which is referenced to the four-dimensional Dixon magnetic resonance imaging data. In other examples the four-dimensional Dixon magnetic resonance imaging data may be divided into bins or groups of data that are then referenced by a particular respiratory signal.

Execution of the machine-executable instructions further causes the processor to reconstruct synthetic four-dimensional computed tomographic image data from the four-dimensional Dixon magnetic resonance imaging data. The four-dimensional Dixon magnetic resonance imaging data is synchronized to the respiratory signal. The reconstruction of the synthetic four-dimensional computed tomographic image data may for example be performed using an algorithm or model that is able to convert a magnetic resonance image into a pseudo-radiographic image.

The use of the four-dimensional Dixon magnetic resonance imaging data for making the synthetic four-dimensional computed tomographic image data may be beneficial because the four-dimensional Dixon magnetic resonance imaging data comprises data which is descriptive primarily of water and fat tissue separately. This may aid in reconstruction of the synthetic four-dimensional computed tomographic image data.

In another embodiment the synthetic four-dimensional computed tomographic image data is synchronized to the respiratory signal. In another embodiment execution of the machine-executable instructions further causes the processor to receive treatment planning data registered to the synthetic four-dimensional computed tomographic image data. The treatment planning data may for example be provided by an automated algorithm. In other examples the treatment planning data may have been entered or provided by a healthcare provider via for example a graphical user interface. The treatment planning data may for example indicate regions of a subject which is desired to deliver a desired radiotherapy dose of radiation. The treatment planning data may also indicate regions, such as sensitive organs or structures, where it is desired to minimize the amount of exposure to radiation.

Execution of the machine-executable instructions further cause the processor to calculate radiotherapy control instructions configured for controlling a radiotherapy system using the treatment planning data, the synthetic four-dimensional computed tomographic image data, and the respiratory signal. The radiotherapy control instructions could for example be calculated using a model that simulates a radiotherapy system. The synthetic four-dimensional computed tomographic image data is useful in simulating the absorption of radiation by the subject. This embodiment therefore provides an improved means of providing radiotherapy control instructions that may be synced to a respiratory signal of the subject.

In another embodiment execution of the machine-executable instructions further causes the processor to first receive treatment planning data and then register the treatment planning data to the synthetic four-dimensional computed tomographic image data. Execution of the machine-executable instructions further cause the processor to calculate radiotherapy control instructions configured for controlling a radiotherapy system using the treatment planning data, the synthetic four-dimensional computed tomographic image data, and the respiratory signal.

In another embodiment the medical system further comprises a magnetic resonance imaging system. The memory further contains simulation pulse sequence commands configured for controlling the magnetic resonance imaging system to acquire simulation magnetic resonance imaging data from an imaging zone according to a four-dimensional magnetic resonance imaging protocol. The term simulation pulse sequence commands are a label to refer to particular pulse sequence commands. During radiation therapy the term simulation is used to refer to a planning phase. The use of the word simulation is then to indicate particular pulse sequence commands that are used for acquiring data for a radiotherapy simulation.

Likewise, the simulation magnetic resonance imaging data is magnetic resonance imaging data that is acquired for the purpose of performing a radiotherapy simulation. The four-dimensional magnetic resonance imaging protocol is a T1 weighted Dixon magnetic resonance imaging protocol. The pulse sequence commands are further configured for acquiring self-navigation k-space data within the simulation magnetic resonance imaging data. The use of the navigation k-space data may be beneficial because this may for example be useful for deriving the respiratory signal and/or measuring motion of the subject during acquisition of the simulation magnetic resonance imaging data. As an alternative to navigation k-space data the respirator signal could be measured using any of the above-mentioned techniques.

Execution of the machine-executable instructions further causes the processor to control the magnetic resonance imaging system with the simulation pulse sequence commands to acquire the simulation magnetic resonance data and the subject respiratory signal. Execution of the machine-executable instructions further causes the processor to determine the respiratory signal using the navigation k-space data. The navigation k-space data is data within the simulation magnetic resonance imaging data.

Execution of the machine-executable instructions further causes the processor to sort the simulation magnetic resonance data into a set of discreet breathing phases using the respiratory signal. Execution of the machine-executable instructions further causes the processor to reconstruct the four-dimensional Dixon magnetic resonance image data from the sorted simulation magnetic resonance data. In this embodiment the simulation magnetic resonance imaging data is acquired and then it is sorted using the respiratory signal as determined by the navigation k-space data.

In another embodiment the medical system further comprises the radiotherapy system. The radiotherapy system is configured for irradiating a target zone within an irradiation zone. The irradiation zone is within the imaging zone. This embodiment is beneficial because the simulation of the radiotherapy may be performed while the subject is in the radiotherapy system. This may be beneficial in that it is less likely that the subject will have moved. Another benefit is that the magnetic resonance imaging system is used to produce the synthetic four-dimensional computed tomographic image data. This may reduce the amount of radiation that the subject is exposed to.

In another embodiment the radiotherapy system is a LINAC system.

In another embodiment the radiotherapy system is an X-ray radiotherapy system.

In another embodiment the radiotherapy system is cobalt radiotherapy system.

In another embodiment the radiotherapy system is a gamma knife.

In another embodiment execution of the machine-executable instructions further causes the processor to control the radiotherapy system with the radiotherapy control instructions to irradiate the target zone. This embodiment may be beneficial because the radiotherapy control instructions may provide for a higher quality radiotherapy system where the irradiation of the target zone is more precisely controlled.

In another embodiment the memory further comprises monitor pulse sequence commands configured for acquiring monitor magnetic resonance imaging data. The monitoring pulse sequence commands are configured for measuring monitor self-navigation k-space data within the monitoring magnetic resonance imaging data. Execution of the machine-executable instructions further causes the processor to acquire the monitor magnetic resonance imaging data during irradiation of the target zone.

Execution of the machine-executable instructions further causes the processor to determine a current respiratory signal using the monitor magnetic resonance imaging data. Execution of the machine-executable instructions further causes the processor to select current magnetic resonance image data from the four-dimensional Dixon magnetic resonance image data using the monitor respiratory signal. Execution of the machine-executable instructions further causes the processor to adjust irradiation of the target zone using the current magnetic resonance image data. This could include gating delivery of the irradiation when the target zone is in the proper location and/or tracking movement of the target zone to adjust targeting of the radiotherapy system. This embodiment may be beneficial because it eliminates the need for an external monitor of subject motion.

In another embodiment the monitor pulse sequence commands are according to the T1 weighted Dixon magnetic resonance imaging protocol. Execution of the machine-executable instructions further causes the processor to repeatedly update an accumulated dose map using the current respiratory signal, the current magnetic resonance image data, and the radiotherapy control instructions. This embodiment may be beneficial because it may provide for a better means of measuring the dosage of irradiation delivered to a subject.

In another embodiment the pulse sequence commands are configured for rotating a k-space sampling pattern between acquisitions of the simulation magnetic resonance imaging data. This embodiment may be beneficial because the central k-space region may for example be used for determining the current respiratory signal. This may also reduce blurring of the four-dimensional Dixon magnetic resonance image data.

In another embodiment the pulse sequence commands are configured for rotating a k-space sampling pattern between acquisitions of the monitor magnetic resonance imaging data. This embodiment may be beneficial because the central k-space region may for example be used for determining the current respiratory signal. This may also reduce blurring of Dixon magnetic resonance image data.

In another embodiment the k-space sampling pattern is a stack of stars k-space sampling pattern or a spiral k-space sampling pattern.

In another embodiment the memory further comprises two-dimensional monitor pulse sequence commands that are configured for acquiring two-dimensional monitor magnetic resonance imaging data. Execution of the machine-executable instructions further cause the processor to acquire the two-dimensional monitor magnetic resonance imaging data during the irradiation of the target zone and execution of the machine-executable instructions further causes the processor to adjust irradiation of the target zone using two-dimensional monitor magnetic resonance imaging data. In this embodiment two-dimensional magnetic resonance images such as are conventionally used are acquired and then used to modify the irradiation. For example, the current position of the subject can be registered to the synthetic four-dimensional computed tomographic image data to modify the control of the radiotherapy system.

In another embodiment the pulse sequence commands are configured for rotating a k-space sampling pattern between acquisitions of the simulation magnetic resonance imaging data. This embodiment may be beneficial because the central region of the rotating k-space pattern may for example be used for self-navigation. It may be further beneficial because the rotation of the k-space sampling pattern allows the k-space data that is acquired to be binned by the respiratory signal.

In another embodiment the k-space sampling pattern is a stack of stars k-space sampling pattern.

In another embodiment the k-space sampling pattern is a spiral k-space sampling pattern.

In another embodiment the four-dimensional Dixon magnetic resonance image data is reconstructed according to a compressed sensing magnetic resonance imaging protocol. Compressed sense reconstructions can also be used in case not all of the magnetic resonance imaging data was acquired. This is true even if the MR acquisition was not set up using compressed sense. If the acquisition of the magnetic resonance imaging data is performed with a time limit, as may be the case in a real time operation, it could happen that not all k-space lines are completely acquired for each breathing phase. A compressed sensing analysis can be useful in compensating for the missing k-space data.

In another embodiment the simulation pulse sequence commands are according to a compressed sensing magnetic resonance imaging protocol. This for example may be beneficial because it may enable the magnetic resonance imaging protocol to be performed more rapidly.

In another embodiment the four-dimensional Dixon magnetic resonance image data comprises a first Dixon image and a second Dixon image for each of the set of discreet breathing phases. The reconstruction of the synthetic four-dimensional computed tomographic image data from the four-dimensional Dixon magnetic resonance imaging data comprises constructing a water Dixon image using the first Dixon image and the second Dixon image for each of the set of discreet breathing phases. The reconstruction of the synthetic four-dimensional computed tomographic image data from the four-dimensional Dixon magnetic resonance imaging data further comprises constructing a fat Dixon image using the first Dixon image and the second Dixon image for each of the set of discreet breathing phases.

The reconstruction of the synthetic four-dimensional computed tomographic image data from the four-dimensional Dixon magnetic resonance imaging data further comprises constructing an in-phase Dixon image using the first Dixon image and the second Dixon image. The reconstruction of the synthetic four-dimensional computed tomographic image data from the four-dimensional Dixon magnetic resonance imaging data further comprises the step of segmenting a body mask for each of the set of discreet breathing phases using the in-phase Dixon image and segmenting a bone mask for each of the set of discreet breathing phases using the in-phase Dixon image. The body mask for instance may be useful in identifying regions which are outside of the subject. For example, regions which are not surrounded by fat or water regions. The bone mask may be represented by regions which lack signal within the body of the subject as defined by the body mask.

Reconstruction of the synthetic four-dimensional computed tomographic image data from the four-dimensional Dixon magnetic resonance imaging data further comprises segmenting regions between the body mask and the bone mask into soft tissue regions for each of the set of discreet breathing phases using the fat Dixon image and the water Dixon image. The use of the fat Dixon image and the water Dixon image may be useful in improving the quality of the segmentation and in differentiating different types of soft tissue.

The reconstruction of the synthetic four-dimensional computed tomographic image data from the four-dimensional Dixon magnetic resonance imaging data further comprises assigning the soft tissue regions a soft tissue Hounsfield unit value for each of the set of discreet breathing phases using a non-rigid registration or using a soft tissue classification model. And then finally, the reconstruction of the synthetic four-dimensional computed tomographic image data from the four-dimensional Dixon magnetic resonance imaging data comprises assigning within the bone mask a bone tissue Hounsfield unit value for each of the set of discreet breathing phases using the non-rigid registration or using a bone tissue classification model. This embodiment may be beneficial because it provides an effective means of producing the synthetic radiographic images from Dixon magnetic resonance images.

In another aspect the invention provides for a computer program product comprising machine-executable instructions for a processor controlling a medical system. Execution of the instructions causes the processor to receive four-dimensional Dixon magnetic resonance image data. The four-dimensional Dixon magnetic resonance image data is T1 weighted. The four-dimensional Dixon magnetic resonance image data is synchronized to a respiratory signal. Execution of the instructions further cause the processor to reconstruct synthetic four-dimensional computed tomographic image data from the four-dimensional Dixon magnetic resonance imaging data. The four-dimensional Dixon magnetic resonance imaging data is synchronized to the respiratory signal. The benefits of this embodiment have been previously discussed.

In another aspect the invention provides for a method of operating a medical system. The method comprises receiving four-dimensional Dixon magnetic resonance image data. The four-dimensional Dixon magnetic resonance imaging data is T1 weighted. The four-dimensional Dixon magnetic resonance image data is synchronized to a respiratory signal.

The method further comprises reconstructing synthetic four-dimensional computed tomographic image data from the four-dimensional Dixon magnetic resonance imaging data. The four-dimensional Dixon magnetic resonance imaging data is synchronized to the respiratory signal. The benefits of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the interne, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code.

References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
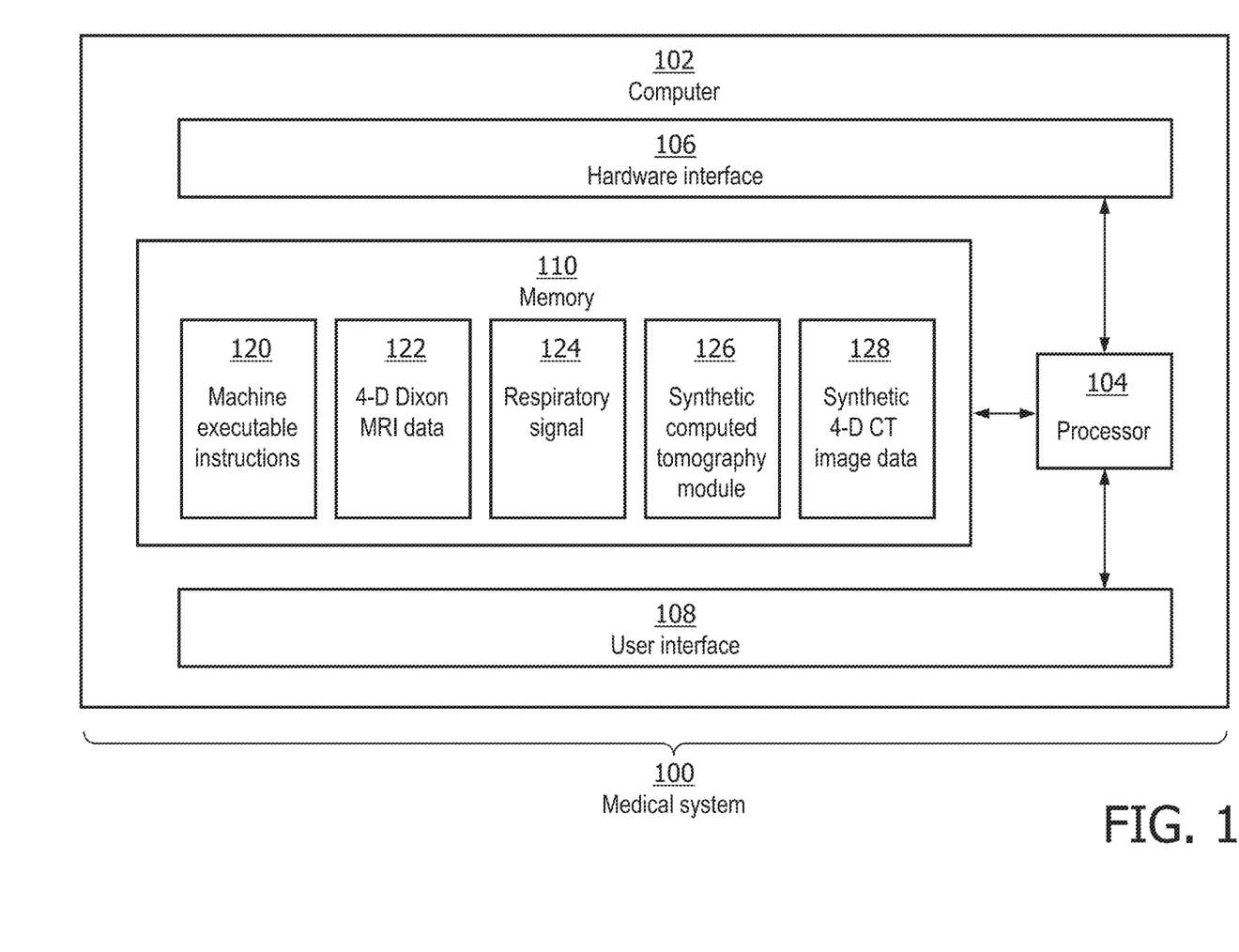
FIG. 1 illustrates an example of a medical instrument.

FIG. 1 illustrates an example of a medical system 100. The medical system 100 is shown as comprising a computer 102. The computer 102 comprises a processor 104. The processor 104 is intended to represent one or more processors with one or more processing cores. The processor 104 could for example be distributed amongst multiple computer systems. The processor 104 is connected to an optional hardware interface. The hardware interface 106 may for example be a network interface that enables the processor 104 to communicate with and/or control additional components of the medical system 100. The processor 104 is further shown as being connected to a user interface 108. The user interface 108 may for example optionally comprise a display, user interface device such as a mouse or keyboard. The user interface 108 may also comprise a graphical user interface.

The processor 104 is shown as being further connected to a memory 110. The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The memory 110 is shown as containing machine-executable instructions 120. The machine-executable instructions 120 enable the processor 104 to perform various control and data analysis techniques. For example, the machine-executable instructions 120 may enable the processor 104 to control other components via the hardware interface 106. The machine-executable instructions 120 also enable the processor 104 to perform various data and image processing techniques. The memory 110 is further shown as containing four-dimensional Dixon magnetic resonance imaging data 122.

The four-dimensional Dixon magnetic resonance imaging data 122 is provided for multiple respiratory phases 124. For example, there may be a number of discreet respiratory phases and for each of these discreet respiratory phases there is a set of four-dimensional Dixon magnetic resonance imaging data 122. The memory 110 is further shown as containing a synthetic computed tomography module 126. This module 126 enables the processor 104 to compute synthetic computed tomography images from Dixon magnetic resonance images. There may for example be a segmentation functionality to the module 126 and other functionalities that enable segmented regions to be assigned a Hounsfield unit.

The memory 110 is further shown as containing a synthetic four-dimensional computed tomographic image data 128 that was reconstructed from the four-dimensional Dixon magnetic resonance imaging data 122 using the synthetic computed tomography module 126. The respiratory signal 124 is also referenced or synced to the synthetic four-dimensional computed tomographic image data 128.

Figure 2:
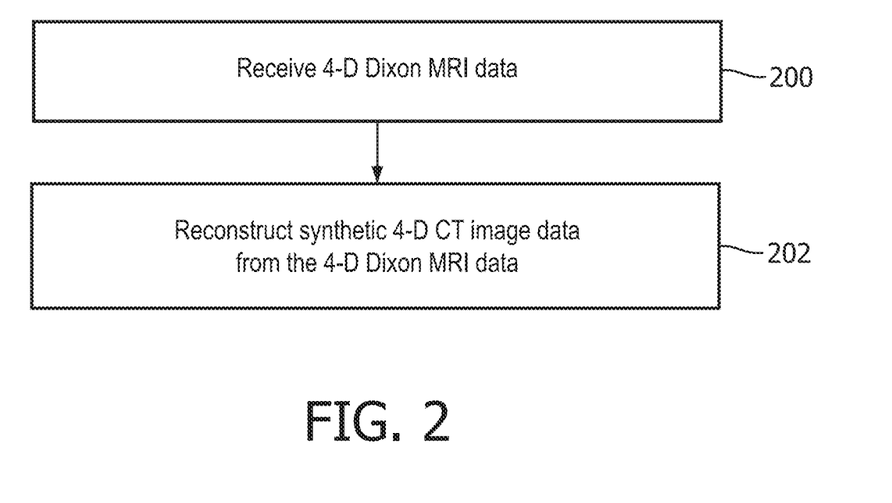
FIG. 2 shows a flow chart which illustrates a method of operating the medical instrument of FIG. 1.

FIG. 2 illustrates a flowchart which provides a method of operating the medical system 100 of FIG. 1. First in step 200 the four-dimensional Dixon magnetic resonance imaging data 122 is received. The four-dimensional Dixon magnetic resonance imaging data 122 is T1 weighted. The four-dimensional Dixon magnetic resonance imaging data is, as was mentioned above, synchronized to the respiratory signal 124. Next in step 202 the synthetic four-dimensional computed tomographic image data 128 is reconstructed from the four-dimensional Dixon magnetic resonance imaging data 122. This may for example be achieved by inputting the four-dimensional Dixon magnetic resonance imaging data 122 into the synthetic computed tomography module 126. The synthetic four-dimensional computed tomographic image data 128 is also synchronized to the respiratory signal 124.

Figure 3:
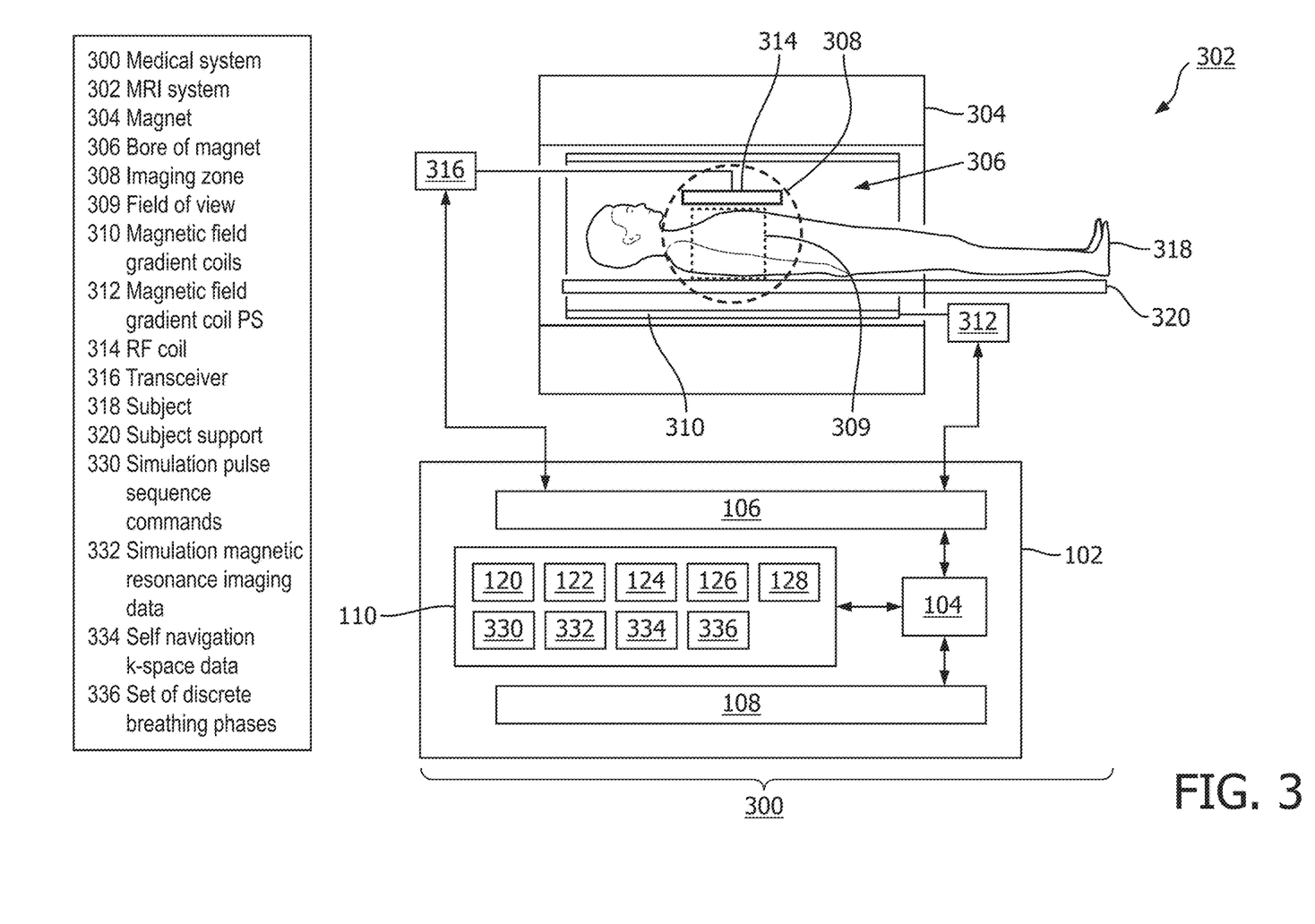
FIG. 3 illustrates a further example of a medical instrument.

FIG. 3 illustrates a further example of a medical system 300. The medical system 300 illustrated in FIG. 3 is similar to that as is illustrated in FIG. 1. The medical system 300 additionally comprises a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections. Some open magnet configurations have one magnet section above the other with a space in-between that is large enough to receive a subject. In another configuration the two magentic sections are arranged adjacent to each other. The the arrangement of the two sections area may be similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A field of view 309 is shown within the imaging zone 308. The magnetic resonance data that is acquired typically acquired for the field of view 309. A subject 318 is shown as being supported by a subject support 320 such that at least a portion of the subject 318 is within the imaging zone 308 and the field of view 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 may also be split to allow radiation to pass. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements. The radio-frequency coil 314 may be designed so that it is effectively radiation transparent: the electronic components and other structures are designed to minimize the amount of radiation scattered or absorbed by the radio-frequency coil 314.

The transceiver 316 and the gradient controller 312 are shown as being connected to the hardware interface 106 of a computer system 102. The memory 110 is further shown as containing simulation pulse sequence commands 330. The simulation pulse sequence commands 330 are configured for acquiring magnetic resonance data according to a Dixon magnetic resonance imaging protocol. The Dixon images are further T1 weighted. The memory 110 is further shown as containing simulation magnetic resonance imaging data 332 that has been acquired by controlling the magnetic resonance imaging system 302 with the simulation pulse sequence commands 330. Embedded within the simulation magnetic resonance imaging data 332 is the self-navigation k-space data 334.

For example, this could be a central k-space region for acquisitions of the simulation magnetic resonance imaging data 332. The self- navigation k-space data 334 can be used to determine the respiratory signal 124. The respiratory signal 124 can then be used to make a set of discreet breathing phases 336. The simulation magnetic resonance imaging data 332 may then be sorted into the set of discreet breathing phases using the breathing phase as determined by the self- navigation k-space data 334. After the simulation magnetic resonance imaging data 332 has been sorted into the set of discreet breathing phases 336 then the four-dimensional Dixon magnetic resonance imaging data 122 can be reconstructed for each of these respiratory phases.

Figure 4:
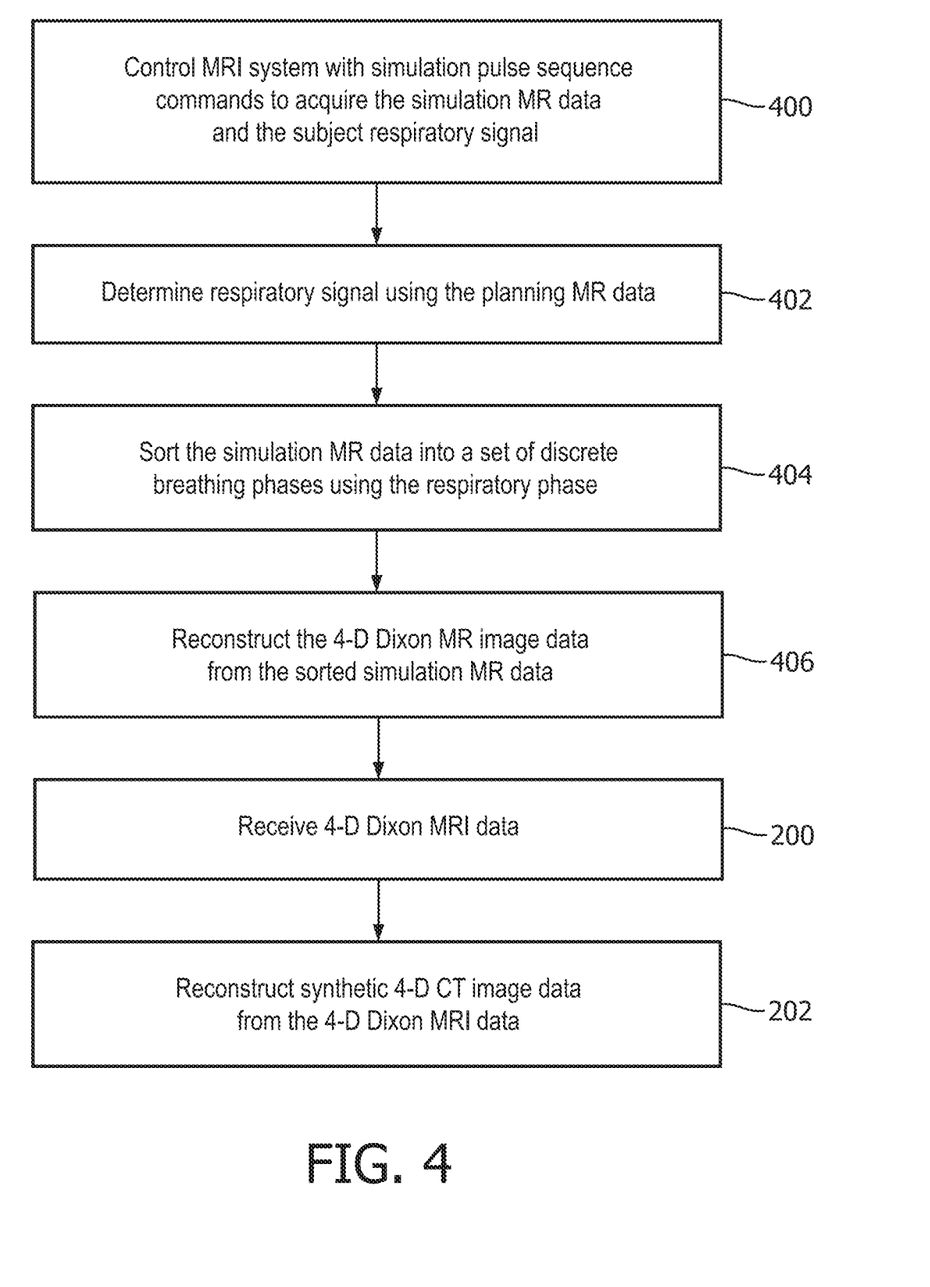
FIG. 4 shows a flow chart which illustrates a method of operating the medical instrument of FIG. 3.

FIG. 4 shows a flowchart which illustrates a method of operating the medical system 300 of FIG. 3. First in step 400 the magnetic resonance imaging system 302 is controlled with the simulation pulse sequence commands 330 to acquire the simulation magnetic resonance imaging data 332. Next in step 402 the respiratory signal 124 is determined using the self-navigation k-space data 334 taken from the simulation magnetic resonance imaging data 332. Next in step 404 the simulation magnetic resonance imaging data 332 is sorted into the set of discreet breathing phases 336. Next in step 406 the four-dimensional Dixon magnetic resonance imaging data 122 is reconstructed from the simulation magnetic resonance imaging data 332 that has been sorted into the set of discreet breathing phases 336. After step 406 the method then proceeds to steps 200 and 202 as is illustrated in FIG. 2.

Figure 5:
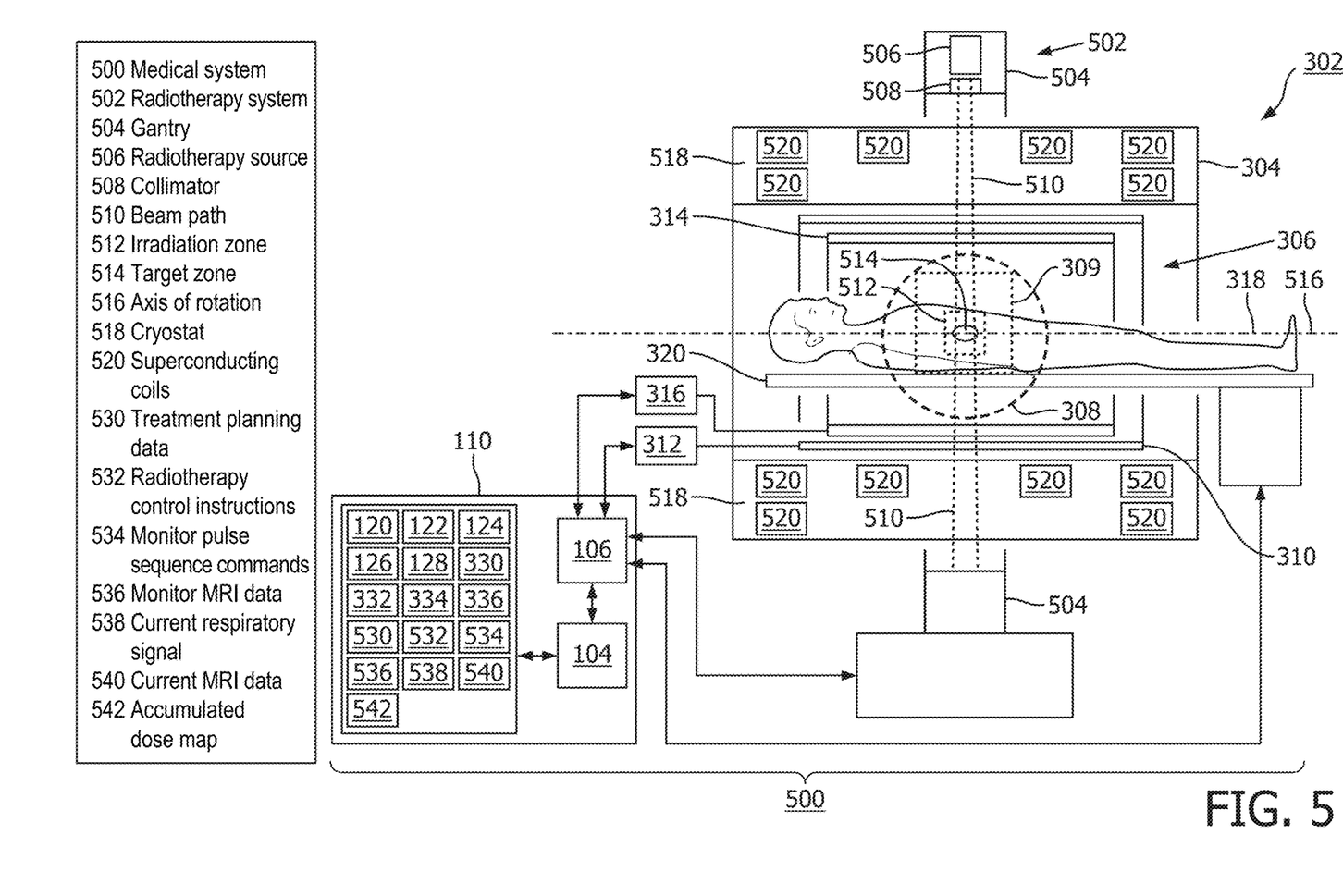
FIG. 5 illustrates a further example of a medical instrument.

FIG. 5 illustrates a further example of a medical system 500. The medical system 500 in FIG. 5 is similar to the medical system 300 depicted in FIG. 3 except that the medical system 500 additionally comprises a radiotherapy system 502. The radiotherapy system 502 is intended to be representative of one of many different types of radiotherapy systems such as a cobalt radiotherapy system, an X-ray radiotherapy system and a LINAC. In this example the radiotherapy system 502 comprises a gantry 504 with a radiotherapy source 506. A collimator 508 may be used to shape a beam path 510. The volume 512 is the irradiation zone and is representative of the volume to which the target zone 514 can be steered. For example, the collimator 508 may be used to adjust the beam path 510. The gantry 504 has an axis of rotation 516 which rotates the radiotherapy source 506 about.

The medical system 500 further comprises the subject support 320 for supporting a subject 318. The subject support 320 is configured such that it can, for example, support a ventral region of the subject 318 in the irradiation zone 512.

The medical system could also comprise breath monitor system, however this is not depicted in the figure. The breath monitor system could be a camera or infra-red camera, an additional MR navigator, a respiratory balloon measurement (measurement of an oxygen mask reservoir), and/or respirator belt. Movement of the subject's 318 chest may be used to generate a motion signal.

The radiotherapy system 502 and the subject support 320 are also shown as being connected to a hardware interface 106 of computer 102. The subject support 320 may for example contain actuators or motors for adjusting the height and position of the subject 318 relative to the axis of rotation 516.

In FIG. 5, the magnetic resonance imaging system 302 and the radiotherapy system 502 are integrated. The radiation zone 512 is within the imaging zone 308. In this example the radiation beam 510 is shown as passing through a cryostat 518 of the magnet 302. The beam avoids the superconducting coils 520. This is intended to be representative. The magnet 304 may also be replaced with a split coil or open magnet so that the radiation beam 510 does not pass through it.

The memory 110 is further shown as containing treatment planning data 530. The treatment planning data 530 is registered to the synthetic four-dimensional computed tomographic image data 128 and/or the four-dimensional Dixon magnetic resonance image data 122. The treatment planning data 530 may be used to indicate regions which are to be irradiated and also indicate regions where the amount of radiation is to be minimized. The treatment planning data 530 in conjunction with the synthetic four-dimensional computed tomographic image data 128 is used to calculate a set of radiotherapy control instructions 532. The radiotherapy control instructions 532 contain commands which control the radiotherapy system 502 to irradiate regions indicated in the treatment planning data 530. The memory 110 is further shown as containing monitor pulse sequence commands 534.

The monitor pulse sequence commands 534 are configured for acquiring monitor magnetic resonance imaging data. The monitor magnetic resonance imaging data 536 contains the self-navigation k-space data. This k-space data can be used to determine a current respiratory signal 538. The current respiratory signal 538 may be used to retrieve current magnetic resonance imaging data 540 from the four-dimensional Dixon magnetic resonance imaging data 122. This magnetic resonance imaging data may then be used to modify the acquisition or the irradiation of the target zone using the current magnetic resonance imaging data.

In some examples the monitor pulse sequence commands are according to the T1 weighted Dixon magnetic resonance imaging protocol. The monitor magnetic resonance imaging data 536 may then be repeatedly acquired during the irradiation of the target zone and this may be used to calculate an accumulated dose map 542 that is very accurate.

Figure 6:
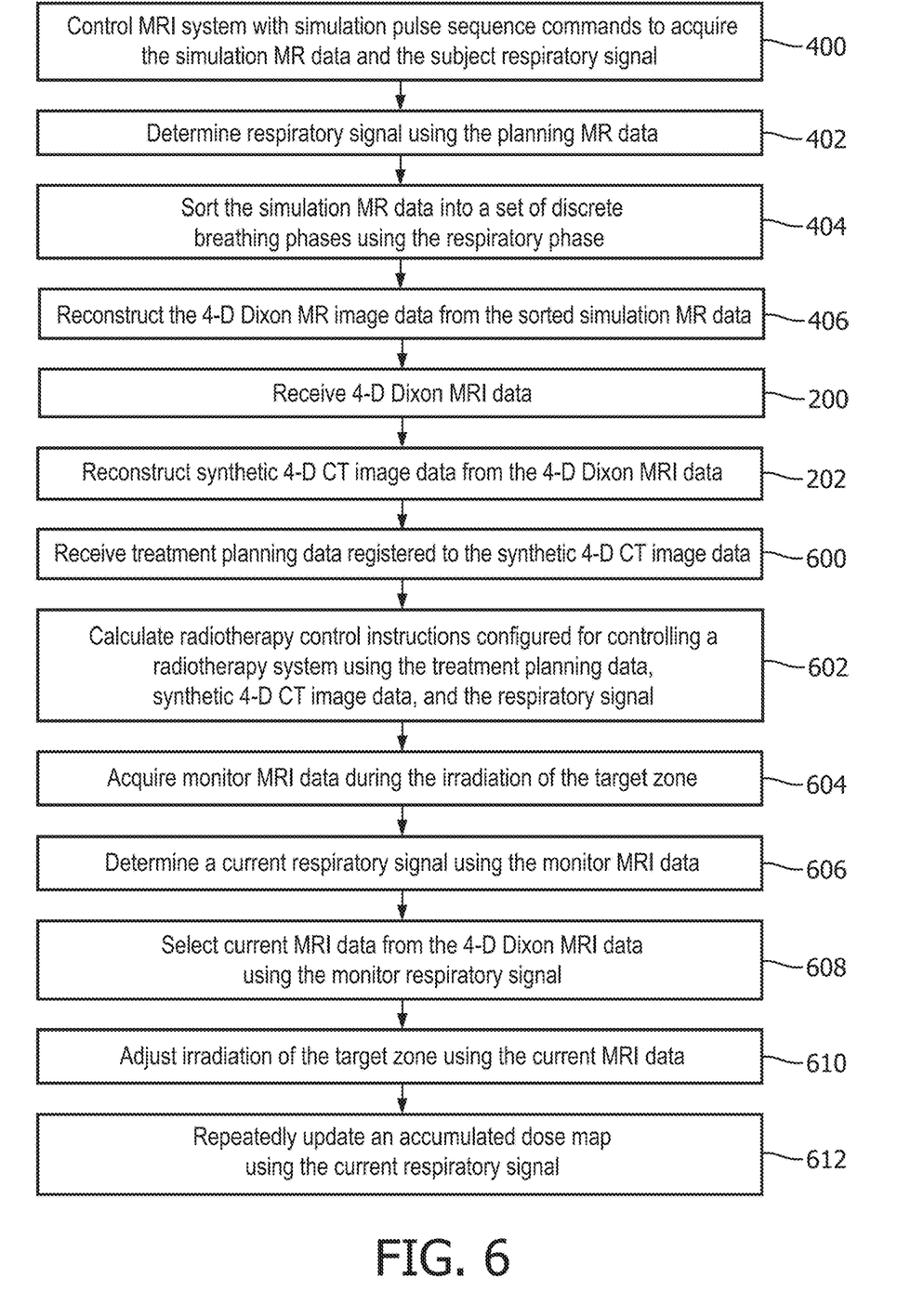
FIG. 6 shows a flow chart which illustrates a method of operating the medical instrument of FIG. 5.

FIG. 6 shows a flowchart that illustrates a method of operating the medical system 500 of FIG. 5. Steps 400-202 as illustrated in FIG. 4 are performed first. The method then proceeds to step 600. In step 600 the treatment planning data 630 is received. The treatment planning data 630 is registered to the synthetic four-dimensional computed tomographic image data 128. Next in step 602 radiotherapy control instructions 632 are calculated for controlling the radiotherapy system 502 using the treatment planning data 630, the synthetic four-dimensional computed tomographic image data 128 and the respiratory signal 124.

As the radiotherapy control instructions 632 are used to control the radiotherapy system 502, the processor controls the magnetic resonance imaging system 302 with the monitor pulse sequence commands 634 to acquire the monitor magnetic resonance imaging data 636. The current respiratory signal 638 can be extracted from the monitor magnetic resonance imaging data 636. In step 606 the current respiratory signal is determined using the self-navigation k-space data that is within the monitor magnetic resonance imaging data 636. Next in step 608 current magnetic resonance image data 640 is selected from the four-dimensional Dixon magnetic resonance image data 122 using the monitor respiratory signal 638. Then in step 610, the irradiation of the target zone is adjusted using the current magnetic resonance image data 640. For example, the current magnetic resonance image data 640 may be registered to what is planned and then a model may be used to generate changes in the radiotherapy control instructions 632. Next in step 612 the accumulated dose map 612 is updated using the current respiratory signal, the current magnetic resonance image data and the radiotherapy control instructions.

Four-dimensional magnetic resonance imaging (4D MRI) has been under development for the past decade for treatment planning to obtain dose calculation information in regions affected by respiratory motion. Examples may provide for a method whereby MR images can be obtained during the radiation to monitor the motion in tumor and organs at risk and generate 4D MRI images. In addition, CT information to be obtained from these images for treatment planning and also dose delivery verification. As a result, 3D volumes can be obtained for each respiratory signal with different image contrasts (water-only, fat-only, in-phase). In this case, it is possible to use the different image contrast with this technique to generate MRCAT images (synthetic computed tomographic images). Examples may have the benefit of generating 4D MRI images in abdomen and thorax plus MRCAT images which can be directly used for MR-only simulation, motion management, dose delivery verification after treatment to optimize the future treatment sessions.

The 4D MRI images (the four-dimensional Dixon magnetic resonance imaging data) may be obtained using a Stack of Star (SOS) radial (e.g. 3D Vane XD) acquisition and XD-GRASP reconstruction (a compressed sensing reconstruction). This approach sorts dynamic data into extra motion-state dimensions using the self-navigation properties of radial imaging and reconstructs the multidimensional dataset using compressed sensing (XD-GRASP). This results in 3D volumes for several respiratory phases and can be used for motion management in treatment planning in radiation oncology.

It is also possible to combine a SOS radial sequence with an mDixon XD sequence (3D Vane mDixon XD—a T1 weighted) to acquire 3D volumes for each respiratory phases (4D MRI) with different image contrasts, thanks to mDixon sequence (water-only 4D MRI, fat-only 4D MRI, in-phase 4D MRI).

Examples may use, the source images obtained by mDixon sequence (water-only, fat-only, in-phase) that are used to classify the tissue into five categories and then assign CT number (Hounsfield Values) to each category to generate synthetic CT images, called MRCAT. As an alternative ratios per pixel for water/fat and spongey/cortical bone can be used to assign the CT number. Another alternative is to use an artificial intelligence module, such as a trained neural network, to assign the CT number.

Examples may use a 3D Vane mDixon XD sequence to obtain 4D MRI images for water, fat, and in-phase contrasts and utilize them as source scan to generate MRCAT images, similar to prostate MRCAT. This technique has the benefit of generating 4D MRI images in abdomen and thorax plus MRCAT images which can be directly used for MR-only simulation on MR-Linac system. In addition, this 4D MRI data can be acquired during the radiation delivery as a motion monitoring technique and to create MRCAT images. The combination of motion monitoring information and MRCAT images can be used for dose delivery verification to ensure the prescribed dose using MR simulation session is accurately delivered to the moving organs during the treatment. Alternatively, the images can be employed for dose planning for the future treatment session.

4D MRI images can be used in MR-Linac for treatment planning to assess the motion in tumor and organs at risks (OARs) to design an accurate treatment plan to reduce the toxicity or OARs and to target the tumor more effectively.

Integrating 4D MRI method with MRCAT using 3D Vane mDixon XD sequence, results in 4D MRI MRCAT images which can overcome the need for CT scan in MR-Linac. Therefore, MR only simulation would be possible in abdomen and thorax with complementary motion information of 4D MRI MRCAT. In addition, CT information generated using 4D MRI MRCAT can be used for dose delivery verification after the treatment delivery.

To achieve this particular example, a first step is to design and optimize a 3D Vane mDixon XD sequence with reasonable image quality and scan time (less than 5 mins). Second step is to incorporate and utilize an XD-GRASP based reconstruction which are binned into 4D MRI images for water, fat, and in-phase images.

The 4D MRI MRCAT can be useful for any anatomies affected with respiratory motion, particularly for upper abdomen (liver, pancreas) and thorax (lung, esophagus). The 4D MRI images can be used to detect the extent of the motion in tumor and OAR and accurately delineates and contours the tumor and clinical target volume (CTV) (target zone 514). MRCAT can be used for an accurate dose calculation using contours drawn on the 4D MRI images. Dose delivery can be also verified after treatment delivery using motion information in 4D MRI and MRCAT images.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 medical system
102 computer
104 processor
106 hardware interface
108 user interface
110 memory
120 machine executable instructions
122 four-dimensional Dixon magnetic resonance imaging data
124 respiratory signal
126 synthetic computed tomography module
128 synthetic four-dimensional computed tomographic image data
200 receive four-dimensional Dixon magnetic resonance image data 202 reconstruct synthetic four-dimensional computed tomographic image data from the four-dimensional Dixon magnetic resonance imaging data
300 medical system
302 magnetic resonance imaging system
304 magnet
306 bore of magnet
308 imaging zone
309 field of view
310 magnetic field gradient coils
312 magnetic field gradient coil power supply
314 radio-frequency coil
316 transceiver
318 subject
320 subject support
330 simulation pulse sequence commands
332 simulation magnetic resonance imaging data
334 self navigation k-space data
336 set of discrete breathing phases
400 control the magnetic resonance imaging system with the simulation pulse sequence commands to acquire the simulation magnetic resonance data and the subject respiratory signal
402 determine the respiratory signal using the planning magnetic resonance data
404 sort the simulation magnetic resonance data into a set of discrete breathing phases using the respiratory phase
406 reconstruct the four-dimensional Dixon magnetic resonance image data from the sorted simulation magnetic resonance data
500 medical system
502 radiotherapy system
504 gantry
506 radiotherapy source
508 collimator
510 beam path
512 irradiation zone
514 target zone
516 axis of rotation
518 cryostat
520 superconducting coils
530 treatment planning data
532 radiotherapy control instructions
534 monitor pulse sequence commands
536 monitor magnetic resonance imaging data
538 current respiratory signal
540 current magnetic resonance imaging data
542 accumulated dose map
600 receive treatment planning data registered to the synthetic four-dimensional computed tomographic image data; and
602 calculate radiotherapy control instructions configured for controlling a radiotherapy system using the treatment planning data, synthetic four-dimensional computed tomographic image data, and the respiratory signal
604 acquire the monitor magnetic resonance imaging data during the irradiation of the target zone
606 determine a current respiratory signal using the monitor magnetic resonance imaging data
608 select current magnetic resonance image data from the four-dimensional Dixon magnetic resonance image data using the monitor respiratory signal
610 adjust irradiation of the target zone using the current magnetic resonance image data
612 repeatedly update an accumulated dose map using the current respiratory signal

The invention claimed is:

1. A medical system comprising:
a processor configured for controlling the medical system;
a memory for storing machine executable instructions, wherein execution of the instructions causes the processor to:
receive four-dimensional Dixon magnetic resonance image data, wherein the four-dimensional Dixon magnetic resonance imaging data is T1 weighted, wherein the four-dimensional Dixon magnetic resonance image data is synchronized to a respiratory signal; and
reconstruct synthetic four-dimensional computed tomographic image data from the four-dimensional Dixon magnetic resonance imaging data, wherein the four-dimensional Dixon magnetic resonance imaging data comprises a first Dixon image and a second Dixon image for each of a set of discrete breathing phases, wherein the reconstruction of the synthetic four-dimensional computed tomographic image data from the four-dimensional Dixon magnetic resonance imaging data comprises:
constructing a water Dixon image using the first Dixon image and the second Dixon image for each of the set of discrete breathing phases;
constructing a fat Dixon image using the first Dixon image and the second Dixon image for each of the set of discrete breathing phases;
constructing an in-phase Dixon image for each of the set of discrete breathing phases using the first Dixon image and the second Dixon image;
segmenting a body mask for each of the set of discrete breathing phases using the in-phase Dixon image;
segmenting a bone mask for each of the set of discrete breathing phases using the in-phase Dixon image;
segmenting regions between the body mask and the bone mask into soft tissue regions for each of the set of discrete breathing phases using the fat Dixon image and the water Dixon image;
assigning the soft tissue regions a soft tissue Hounsfield Unit value for each of the set of discrete breathing phases using a non-rigid registration or using a soft tissue classification model; and
assigning within the bone mask a bone tissue Hounsfield Unit value for each of the set of discrete breathing phases using the non-rigid registration or using a bone tissue classification model.

2. The medical system of claim 1, wherein execution of the machine executable instructions further causes the processor to: receive treatment planning data registered to the synthetic four-dimensional computed tomographic image data; and calculate radiotherapy control instructions configured for controlling a radiotherapy system using the treatment planning data, the synthetic four-dimensional computed tomographic image data, and the respiratory signal.

3. The medical system of claim 2, wherein the medical system further comprises a magnetic resonance imaging system wherein the memory further contains simulation pulse sequence commands configured for controlling the magnetic resonance imaging system to acquire simulation magnetic resonance imaging data from an imaging zone fee, according to a four-dimensional magnetic resonance imaging protocol, wherein the four-dimensional magnetic resonance imaging protocol is a T1 weighted Dixon magnetic resonance imaging protocol, wherein the pulse sequence commands are further configured for acquiring self-navigation k-space data within the simulation magnetic resonance imaging data, wherein execution of the machine executable instructions further causes the processor to:

control the magnetic resonance imaging system with the simulation pulse sequence commands to acquire the simulation magnetic resonance data and the respiratory signal;

determine the respiratory signal using the self-navigation k-space data;

sort the simulation magnetic resonance data into the set of discrete breathing phases using the respiratory signal; and reconstruct the four-dimensional Dixon magnetic resonance image data from the sorted simulation magnetic resonance data.

4. The medical system of claim 3, wherein the medical system further comprises the radiotherapy system, wherein the radiotherapy system is configured for controllably irradiating a target zone within an irradiation zone, and wherein the irradiation zone is within the imaging zone.

5. The medical system of claim 4, wherein the radiotherapy system is any one of the following: a linear accelerator (LINAC), an X-ray radiotherapy system, a gamma knife, and a cobalt radiotherapy system.

6. The medical system of claim 4, wherein execution of the machine executable instructions further causes the processor to control the radiotherapy system with the radiotherapy control instructions to irradiate the target zone.

7. The medical system of claim 6, wherein the memory further comprises monitor pulse sequence commands configured for acquiring monitor magnetic resonance imaging data, wherein the monitoring pulse sequence commands are configured for measuring monitor self-navigation k-space data within the monitor magnetic resonance imaging data, wherein execution of the machine executable instructions further causes the processor to:

acquire the monitor magnetic resonance imaging data during the irradiation of the target zone;

determine a current respiratory signal using the monitor magnetic resonance imaging data;

select current magnetic resonance image data from the four-dimensional Dixon magnetic resonance image data using the current respiratory signal; and adjust irradiation of the target zone using the current magnetic resonance image data.

8. The medical system of claim 6, wherein the monitor pulse sequence commands are according to the T1 weighted Dixon magnetic resonance imaging protocol wherein execution of the machine executable instructions further causes the processor to repeatedly update an accumulated radiation dose map using the current respiratory signal, the current magnetic resonance image data, and the radiotherapy control instructions.

9. The medical system of claim 6, wherein the memory further comprises two-dimensional monitor pulse sequence commands configured for acquiring two-dimensional monitor magnetic resonance imaging data, wherein execution of the machine executable instructions further causes the processor to:

acquire the two-dimensional monitor magnetic resonance imaging data during the irradiation of the target zone; and adjust irradiation of the target zone using two-dimensional monitor magnetic resonance imaging data.

10. The medical system of claim 3, wherein the pulse sequence commands are configured for rotating a k-space sampling pattern between acquisitions of the simulation magnetic resonance imaging data.

11. The medical system of claim 10, wherein the k-space sampling pattern any one of the following: a stack-of-stars k-space sampling pattern and a spiral k-space sampling pattern.

12. The medical system of claim 3, wherein the four-dimensional Dixon magnetic resonance imaging data is reconstructed.

13. A non-transitory computer readable medium comprising machine executable instructions for a processor controlling a medical system, wherein execution of the instructions causes the processor to:

receive four-dimensional Dixon magnetic resonance image data wherein the four-dimensional Dixon magnetic resonance imaging data is T1 weighted, wherein the four-dimensional Dixon magnetic resonance image data is synchronized to a respiratory signal; and reconstruct synthetic four-dimensional computed tomographic image data from the four-dimensional Dixon magnetic resonance imaging data, wherein the four-dimensional Dixon magnetic resonance imaging data comprises a first Dixon image and a second Dixon image for each of a set of discrete breathing phases, wherein the reconstruction of the synthetic four-dimensional computed tomographic image data from the four-dimensional Dixon magnetic resonance imaging data comprises:

constructing a water Dixon image using the first Dixon image and the second Dixon image for each of the set of discrete breathing phases;

constructing a fat Dixon image using the first Dixon image and the second Dixon image for each of the set of discrete breathing phases;

constructing an in-phase Dixon image for each of the set of discrete breathing phases using the first Dixon image and the second Dixon image;

segmenting a body mask for each of the set of discrete breathing phases using the in-phase Dixon image;

segmenting a bone mask for each of the set of discrete breathing phases using the in-phase Dixon image;

segmenting regions between the body mask and the bone mask into soft tissue regions for each of the set of discrete breathing phases using the fat Dixon image and the water Dixon image;

assigning the soft tissue regions a soft tissue Hounsfield Unit value for each of the set of discrete breathing phases using a non-rigid registration or using a soft tissue classification model; and assigning within the bone mask a bone tissue Hounsfield Unit value for each of the set of discrete breathing phases using the non-rigid registration or using a bone tissue classification model.

14. A method of operating a medical system wherein the method comprises:

receiving four-dimensional Dixon magnetic resonance image data wherein the four-dimensional Dixon magnetic resonance imaging data is T1 weighted, wherein the four-dimensional Dixon magnetic resonance image data is synchronized to a respiratory signal; and reconstructing synthetic four-dimensional computed tomographic image data from the four-dimensional Dixon magnetic resonance imaging data, wherein the four-dimensional Dixon magnetic resonance imaging data comprises a first Dixon image and a second Dixon image for each of a set of discrete breathing phases, wherein the reconstruction of the synthetic four-dimensional computed tomographic image data from the four-dimensional Dixon magnetic resonance imaging data comprises:

constructing a water Dixon image using the first Dixon image and the second Dixon image for each of the set of discrete breathing phases;

constructing a fat Dixon image using the first Dixon image and the second Dixon image for each of the set of discrete breathing phases;

constructing an in-phase Dixon image using the first Dixon image and the second Dixon image;

segmenting a body mask for each of the set of discrete breathing phases using the in-phase Dixon image;

segmenting a bone mask for each of the set of discrete breathing phases using the in-phase Dixon image;

segmenting regions between the body mask and the bone mask into soft tissue regions for each of the set of discrete breathing phases using the fat Dixon image and the water Dixon image;

assigning the soft tissue regions a soft tissue Hounsfield Unit value for each of the set of discrete breathing phases using a non-rigid registration or using a soft tissue classification model; and assigning within the bone mask a bone tissue Hounsfield Unit value for each of the set of discrete breathing phases using the non-rigid registration or using a bone tissue classification model.

\* \* \* \* \*